US011472845B2

(12) United States Patent
Baileykobayashi et al.

(10) Patent No.: US 11,472,845 B2
(45) Date of Patent: Oct. 18, 2022

(54) ANTITUMOR PEPTIDE AND USE THEREOF

(71) Applicants: TOAGOSEI CO., LTD., Tokyo (JP); The University of Tokyo, Tokyo (JP)

(72) Inventors: Nahoko Baileykobayashi, Tsukuba (JP); Tetsuhiko Yoshida, Tsukuba (JP); Shuichi Asakawa, Bunkyo-Ku (JP)

(73) Assignees: TOAGOSEI CO., LTD, Tokyo (JP); The University of Tokyo, Tokyo (JP)

(*) Notice: Subject to any disclaimer, the term of this patent is extended or adjusted under 35 U.S.C. 154(b) by 7 days.

(21) Appl. No.: 17/065,838

(22) Filed: Oct. 8, 2020

(65) Prior Publication Data

US 2021/0115089 A1 Apr. 22, 2021

(30) Foreign Application Priority Data

Oct. 21, 2019 (JP) .............................. JP2019-191920

(51) Int. Cl.
*C07K 14/00* (2006.01)
*A61P 35/00* (2006.01)
*A61K 38/00* (2006.01)

(52) U.S. Cl.
CPC ............ *C07K 14/001* (2013.01); *A61P 35/00* (2018.01); *A61K 38/00* (2013.01)

(58) Field of Classification Search
CPC ........ C07K 14/001; A61P 35/00; A61K 38/00
See application file for complete search history.

(56) References Cited

FOREIGN PATENT DOCUMENTS

WO     2000032231 A1     6/2000
WO     WO-2009058564 A2 *  5/2009 ........ C07K 14/70521

OTHER PUBLICATIONS

Maeda H and Khatami M "Analyses of repeated failures in cancer therapy for solid tumors: poor tumor-selective drug delivery, low therapeutic efficacy and unsustainable costs" Clin Trans Med 7:11 (Year: 2018).*
Ott, Patrick A. "CTLA-4 and PD-1/PD-L1 Blockade: New Immunotherapeutic Modalities with Durable Clinical Benefit in Melanoma Patients" Clinical Cancer Research , vol. 19, No. 19, 2013, pp. 5300-5309.

* cited by examiner

*Primary Examiner* — Sudhakar Katakam
*Assistant Examiner* — Zachary J Miknis
(74) *Attorney, Agent, or Firm* — Occhiuti & Rohlicek LLP

(57) ABSTRACT

A synthetic peptide provided by the present invention includes: (1) a CTLA4-SP-related sequence; and (2) an amino acid sequence that functions as a cell penetrating peptide, wherein the synthetic peptide has a total number of amino acid residues of 100 or less.

8 Claims, No Drawings

Specification includes a Sequence Listing.

ANTITUMOR PEPTIDE AND USE THEREOF

CROSS-REFERENCE TO RELATED APPLICATIONS

Priority is claimed on Japanese Patent Application No. 2019-191920, filed Oct. 21, 2019, the content of which is incorporated herein by reference.

TECHNICAL FIELD

The present invention relates to an artificially synthesized antitumor peptide that can inhibit proliferation of tumor cells and use thereof. The present invention specifically relates to use of a synthetic peptide including an amino acid sequence constituting a signal peptide of cytotoxic T lymphocyte antigen-4 (CTLA4) and a cell-penetrating peptide sequence.

TECHNICAL BACKGROUND

In recent years, basic research and clinical research regarding "immunotherapy" for cancer using functions of an immune monitoring mechanism have been actively conducted.

Cancerous cells (cancer cells, tumor cells) are recognized as foreign substances in a living body and can be eliminated by an immune monitoring mechanism. However, if functions of the immune monitoring mechanism are inhibited, tumor cells can avoid attack by the immune monitoring mechanism and proliferate. As a result, tumor tissues grow larger. Examples of factors that inhibit functions of the immune monitoring mechanism include inhibition of T cell activation and inhibition of proliferation of cytotoxic T cells that attack tumor cells.

Activation of T cells is controlled by, for example, signals through T cell receptors (TCRs) and costimulatory receptors. For example, when antigen-presenting cells (dendritic cells, etc.) that present a tumor antigen transmit tumor antigen information to T cells through TCRs, CD80/CD86 on antigen-presenting cells binds to CD28 which is one costimulatory receptor on T cells. Then, an activation signal is transmitted to T cells.

T cells express cytotoxic T lymphocyte antigen-4 (CTLA4) as another costimulatory receptor. CTLA4 can bind to the above CD80/CD86. Since CTLA4 has an inhibitory motif as an intracellular domain, the above binding causes T cells to generate an inhibitory signal. Thus, when activation of T cells is inhibited by the binding between CTLA4 and CD80/CD86, proliferation of cytotoxic T cells is inhibited. Accordingly, removal of tumor cells can be inhibited. Therefore, this can be a factor that promotes spread of tumor tissues.

Incidentally, CTLA4 has become an important target in current cancer immunotherapy. The binding between CTLA4 and CD80/CD86 is inhibited by anti-CTLA4 antibodies, and thus the above T cell activation inhibition and cytotoxic T cell proliferation inhibition are removed. It is confirmed in Patent Literature (WO 2000/32231) that proliferation of some tumors is inhibited by administering anti-CTLA4 antibodies. In addition, in Non Patent Literature (CTLA-4 and PD-1/PD-L1 Blockade: New Immunotherapeutic Modalities with Durable Clinical Benefit in Melanoma Patients, 2013, Clinical Cancer Research, 19, 5300-5309), anti-CTLA4 antibodies are clinically used as a therapeutic agent.

The action mechanism of anti-CTLA4 antibodies is not limited to removal of T cell activation inhibition and cytotoxic T cell proliferation inhibition based on inhibition of the binding between CTLA4 and CD80/CD86 as described above. Examples of other action mechanisms include regulatory T cell (Treg) function inhibition and removal of Treg.

When Treg functions in tumor tissues, for example, removal of tumor cells by cytotoxic T cells is inhibited. It is known that Treg also expresses CTLA4 and the function is inhibited by CTLA4-mediated stimulation. The anti-CTLA4 antibody can inhibit the function of Treg (that is, cytotoxic T cell function inhibition) by stimulating CTLA4 expressed on Treg. In addition, the anti-CTLA4 antibody can remove Treg from tumor tissues by antibody-dependent cytotoxic activity based on the binding to CTLA4 on Treg.

Anti-CTLA4 antibodies as a therapeutic agent have a plurality of action mechanisms as described above and clinical effects are also actually recognized. However, such antibody drugs are extremely expensive. Therefore, the cost of a cancer treatment becomes a serious problem due to the treatment using the therapeutic agent.

Here, an object (purpose) of the present invention is to provide a synthetic peptide having a configuration different from that of an antitumor agent using expensive antibodies and having antitumor (anticancer) properties.

SUMMARY OF THE INVENTION

The inventors have focused on a signal peptide of CTLA4 expressed in many species, particularly mammals. Thus, the inventors surprisingly found that a synthetic peptide in which amino acid sequences constituting a signal peptide of CTLA4 and amino acid sequences constituting a conventionally known cell penetrating peptide (CPP) are combined has excellent antitumor properties (anticancer properties) with respect to various tumor cells, and thereby completed the present invention.

Specifically, the synthetic peptide disclosed here is a synthetic peptide that inhibits proliferation of at least one type of tumor cells. The peptide includes the following amino acid sequences (1) and (2):
(1) a CTLA4-SP-related sequence composed of an amino acid sequence constituting a signal peptide (SP) of cytotoxic T lymphocyte antigen-4 (CTLA4) or a modified amino acid sequence in which one, two, or three amino acid residues are deleted, replaced or added in the amino acid sequence; and
(2) a CPP-related sequence composed of an amino acid sequence that functions as a cell-penetrating peptide (CPP).

In a preferable aspect, the synthetic peptide disclosed here has a total number of amino acid residues of 100 or less. In consideration of production costs, ease of synthesis, and handling properties, more preferably, the total number of amino acid residues is 80 or less (for example, 70 or less).

Alternatively, a synthetic peptide in which a proportion of the amino acid sequence shown in (1) and the amino acid sequence shown in (2) is 80 number % or more (more preferably 90 number % or more, for example, 100 number %) of the total amino acids of the synthetic peptide is a particularly suitable aspect among the synthetic peptides disclosed here.

In a preferable aspect, in the synthetic peptide disclosed here, the CTLA4-SP-related sequence is an amino acid sequence represented by any one of SEQ ID NOs: 1 to 8.

In addition, in another suitable aspect of the synthetic peptide disclosed here, the CPP-related sequence is a polyarginine (not particularly limited, but typically composed of 5 or more and 9 or less arginine residues), or an amino acid sequence represented by any one of SEQ ID NOs: 9 to 26.

In another suitable aspect of the synthetic peptide disclosed here, the CPP-related sequence is adjacent to the N-terminal or C-terminal side of the CTLA4-SP-related sequence. Alternatively, the CPP-related sequence is arranged on the N-terminal or C-terminal side via a linker composed of 10 or less (preferably, 5 or less, for example, 1 or 2) amino acid residues.

In a preferable aspect, the synthetic peptide disclosed here includes an amino acid sequence represented by SEQ ID NO: 27.

In addition, the present invention provides an antitumor composition that inhibits proliferation of at least one type of tumor cells, the antitumor composition including any of the synthetic peptides (antitumor peptides) disclosed here and at least one pharmaceutically acceptable carrier.

Such a composition that contains the synthetic peptide disclosed here can be used as an antitumor agent (including an anticancer agent; the same applies hereinafter) or a material for development of a novel antitumor agent.

In addition, the present invention provides a method of inhibiting proliferation of at least one type of tumor cells, the method including supplying any of the synthetic peptides (antitumor peptides) disclosed here to target tumor cells (for example, outside a living organism=in vitro or inside a living organism=in vivo) at least once.

In the method in such a configuration, when the synthetic peptide disclosed here is supplied to tumor cells, it is possible to prevent or inhibit proliferation of tumor cells (preferably, further enlargement in tumor or cancer tissues).

DESCRIPTION OF THE RELATED EMBODIMENTS

Preferable embodiments of the present invention will be described below. Components other than those particularly mentioned in this specification (for example, the primary structure and chain length of the synthetic peptide disclosed here) that are necessary for implementation of the present invention (for example, a method of chemically synthesizing a peptide, a cell culture technique, and a general method of preparing a pharmaceutical composition including a peptide as a component) can be recognized by those skilled in the art as design matters based on the related art in the fields of cell engineering, physiology, medicine, pharmacy, organic chemistry, biochemistry, genetic engineering, protein engineering, molecular biology, genetics, and the like. The present invention can be implemented based on content disclosed in this specification and common general technical knowledge in the field. Here, in the following description, amino acids are represented by one-letter symbols (but three-letter symbols in the sequence listing).

The entire content of all documents cited in this specification is incorporated herein by reference.

In this specification, "tumor" is a term that is interpreted in a broad sense, and refers to a general tumor (typically, a malignant tumor) such as a carcinoma or sarcoma or blood or hematopoietic tissue lesions (leukemia, lymphoma, etc.). In addition, "tumor cell" is the same as "cancer cell" and refers to cells that form such a tumor and cells (so-called cancerous cells) that typically abnormally proliferate regardless of surrounding normal tissues. Therefore, unless otherwise specified, cells that are classified as tumor cells (cancer cells) rather than normal cells are referred to as tumor cells regardless of the origin or properties of the cells. Cells constituting epithelial tumors (squamous cell carcinoma, adenocarcinoma, etc.), non-epithelial tumors (various sarcomas and osteosarcomas, etc.), various cell tumors (neuroblastoma, retinoblastoma, etc.), lymphoma, melanoma, or the like are typical examples included among the tumor cells mentioned here.

In addition, "synthetic peptide" in this specification refers to a peptide fragment of which a peptide chain alone is not independently and stably present in nature, but is produced through artificial chemical synthesis or biosynthesis (that is, production based on genetic engineering) and can be stably present in a predetermined composition. Here, the term "peptide" refers to an amino acid polymer having a plurality of peptide bonds, and although the number of amino acid residues included in the peptide chain is not limited, the peptide is a relatively low-molecular-weight polymer, typically with a total number of amino acid residues of about 100 or less (preferably 80 or less, more preferably 70 or less, and particularly preferably 60 or less).

In addition, the term "amino acid residue" in this specification refers to an N-terminal amino acid or a C-terminal amino acid of a peptide chain unless otherwise specified.

Here, the left side of the amino acid sequences described in this specification is always the N-terminal side, and the right side thereof is always the C-terminal side.

"Modified amino acid sequence" with respect to a predetermined amino acid sequence in this specification refers to an amino acid sequence formed when one or more (typically, 9 or less, and preferably 5 or less) amino acid residues, for example, one, two, or three amino acid residues, are replaced, deleted or added (inserted) without impairing functions (for example, antitumor activity and cell membrane penetrating ability) of the predetermined amino acid sequence. For example, a sequence generated by so-called conservative replacement (conservative amino acid replacement) in which one, two, or three amino acid residues are conservatively replaced (for example, a sequence in which a basic amino acid residue is replaced with another basic amino acid residue: for example, a lysine residue and an arginine residue are replaced with each other), a sequence in which one, two, or three amino acid residues are added (inserted) to or deleted from a predetermined amino acid sequence, and the like are typical examples included among the modified amino acid sequences referred to in this specification. Accordingly, the synthetic peptide disclosed as an example here may be, in addition to a synthetic peptide composed of the same amino acid sequences as the amino acid sequences of SEQ ID NOs, synthetic peptides composed of modified amino acid sequences in which one, two, or three amino acid residues are replaced (for example, the above conservative replacement), deleted or added in amino acid sequences of SEQ ID NOs which are amino acid sequences exhibiting the same antitumor activity.

The artificially synthesized synthetic peptide disclosed here is a short chain peptide that does not occur in nature and that the inventors found to inhibit proliferation of tumor cells (that is, antitumor activity), and is a peptide including the above two amino acid sequences, that is,
(1) a CTLA4-SP-related sequence and
(2) a CPP-related sequence.

Here, the CTLA4-SP-related sequence is an amino acid sequence which constitutes a signal peptide (SP) of proteins constituting cytotoxic T lymphocyte antigen-4 (CTLA4) or a modified amino acid sequence thereof.

CTLA4 is a membrane protein composed of typically about 223 amino acid residues (UniProtKB-P16410). It is described in the above Patent Literature and Non Patent Literature that CTLA4 is expressed on the surface of T cells, and for example, has a function as a negative modulator that inhibits excess T cell activation by binding to CD80/CD86 that is expressed on the surface of antigen-presenting cells (dendritic cells, etc.).

However, it has not been found that the signal peptide of CTLA4 itself has antitumor activity, and the fact that an artificially synthesized antitumor peptide is obtained by synthesizing an amino acid sequence of such a signal peptide and adding a CPP to the sequence was completely unexpected at the time of filing this application.

Information on genes (including the case of cDNA) encoding CTLA4 and amino acid sequence information can be obtained by accessing knowledge bases (databases) in various public international organizations. For example, all amino acid sequence information of CTLA4 derived from various species and amino acid sequence information of the signal peptide can be obtained in Universal Protein Resource (UniProt). According to the database, at least information on CTLA4 in mammals such as humans, dogs, mice, rabbits, and pigs can be obtained.

The CTLA4-SP-related sequences according to the above (1) preferably used for implementing the present invention are shown in, for example, SEQ ID NOs: 1 to 8.

Specifically, the amino acid sequence of SEQ ID NO: 1 is an amino acid sequence composed of a total of 35 amino acid residues constituting a signal peptide of human (*Homo sapiens*)-derived CTLA4.

Here, in the SEQ ID NO: 1, the amino acid sequence constituting a signal peptide of human-derived CTLA4 is shown, but the sequence is only an example, and available amino acid sequences are not limited thereto.

The amino acid sequence of SEQ ID NO: 2 is an amino acid sequence composed of a total of 35 amino acid residues constituting a signal peptide of dog (*Canis familiaris*)-derived CTLA4 (UniProtKB-Q9XSI1).

In addition, the amino acid sequence of SEQ ID NO: 3 is an amino acid sequence composed of a total of 35 amino acid residues constituting a signal peptide of mouse (*Mus musculus*)-derived CTLA4 (UniProtKB-P09793).

In addition, the amino acid sequence of SEQ ID NO: 4 is an amino acid sequence composed of a total of 35 amino acid residues constituting a signal peptide of rabbit (*Oryctilagus cuniculus*)-derived CTLA4 (UniProtKB-42072).

In addition, the amino acid sequence of SEQ ID NO: 5 is an amino acid sequence composed of a total of 35 amino acid residues constituting a signal peptide of pig (*Sus scrofa*)-derived CTLA4 (UniProtKB-Q9MYX7).

Here, information on genes (including the case of cDNA) encoding CTLA4 and amino acid sequence information can be acquired from the National Center for Biotechnology Information (NCBI).

The amino acid sequence of SEQ ID NO: 6 is an amino acid sequence composed of a total of 37 amino acid residues constituting a signal peptide of night monkey (*Aotus trivirgatus*)-derived CTLA4 (GenBank: AAK37530.1).

The amino acid sequence of SEQ ID NO: 7 is an amino acid sequence composed of a total of 37 amino acid residues constituting a signal peptide of Anubis baboon (*Papio anubis*)-derived CTLA4 (NP_001106104.1).

The amino acid sequence of SEQ ID NO: 8 is an amino acid sequence composed of a total of 37 amino acid residues constituting a signal peptide of rhesus macaque (*Macaca mulatta*)-derived CTLA4 (NP_001038204.1).

Any of the amino acid sequences shown in the above SEQ ID NOs: 1 to 8 can be preferably used as the CTLA4-SP-related sequence.

Regarding an amino acid sequence (that is, a CPP-related sequence) that functions as a CPP that is used to construct a synthetic peptide disclosed here, various conventional known CPPs can be used. For example, a so-called polyarginine (Rn) composed of 3 or more, preferably 5 or more and 11 or less, preferably 9 or less arginine residues, is suitable as a CPP used here. In addition, various known CPPs can be used.

Although not particularly limited, SEQ ID NOs: 9 to 26 are preferable examples of an amino acid sequence that functions as a CPP. Specifically, SEQ ID NOs: 9 to 26 are as follows.

The amino acid sequence of SEQ ID NO: 9 corresponds to nucleolar localization signal (NoLS) composed of a total of 14 amino acid residues derived from basic fibroblast growth factor (FGF2).

The amino acid sequence of SEQ ID NO: 10 corresponds to NoLS composed of a total of 19 amino acid residues derived from one type (ApLLP) of nucleolar proteins.

The amino acid sequence of SEQ ID NO: 11 corresponds to NoLS composed of a total of 16 amino acid residues derived from a protein ($\gamma(1)$ 34.5) of herpes simplex virus type 1 (HSV-1).

The amino acid sequence of SEQ ID NO: 12 corresponds to NoLS composed of a total of 19 amino acid residues derived from a p40 protein of human I-mfa domain-containing protein (HIC).

The amino acid sequence of SEQ ID NO: 13 corresponds to NoLS composed of a total of 16 amino acid residues derived from an MEQ protein of Marek disease virus (MDV).

The amino acid sequence of SEQ ID NO: 14 corresponds to NoLS composed of a total of 17 amino acid residues derived from Survivin-deltaEx3 which is a protein that inhibits apoptosis.

The amino acid sequence of SEQ ID NO: 15 corresponds to NoLS composed of a total of 7 amino acid residues derived from Angiogenin which is a vascular growth factor.

The amino acid sequence of SEQ ID NO: 16 corresponds to NoLS composed of a total of 8 amino acid residues derived from MDM2 which is a nuclear phosphoprotein and forms a complex with the p53 tumor suppression protein.

The amino acid sequence of SEQ ID NO: 17 corresponds to NoLS composed of a total of 9 amino acid residues derived from GGNNVα which is a betanodaviral protein.

The amino acid sequence of SEQ ID NO: 18 corresponds to NoLS composed of a total of 7 amino acid residues derived from NF-κB inducible kinase (NIK).

The amino acid sequence of SEQ ID NO: 19 corresponds to NoLS composed of a total of 15 amino acid residues derived from nuclear VCP-like protein.

The amino acid sequence of SEQ ID NO: 20 corresponds to NoLS composed of a total of 18 amino acid residues derived from p120 which is a nucleolar protein.

The amino acid sequence of SEQ ID NO: 21 corresponds to NoLS composed of a total of 14 amino acid residues derived from an ORF57 protein of herpes virus saimiri (HVS).

The amino acid sequence of SEQ ID NO: 22 corresponds to NoLS composed of a total of 13 amino acid residues from the 491st amino acid residue of kinase 2 (LIM Kinase 2) present in human endothelial cells, which is one protein kinase related to intracellular information transfer, to the 503rd amino acid residue.

The amino acid sequence of SEQ ID NO: 23 corresponds to NoLS composed of a total of 8 amino acid residues included in the nucleocapsid protein (N protein) of avian infectious bronchitis virus (IBV).

The amino acid sequence of SEQ ID NO: 24 corresponds to a membrane-penetrating motif composed of a total of 9 amino acid sequences derived from a protein transduction domain included in TAT of human immunodeficiency virus (HIV).

The amino acid sequence of SEQ ID NO: 25 corresponds to a membrane-penetrating motif composed of a total of 11 amino acid sequences of the protein transduction domain (PTD4) obtained by modifying the above TAT.

The amino acid sequence of SEQ ID NO: 26 corresponds to a membrane-penetrating motif composed of a total of 18 amino acid sequences derived from ANT of Antennapedia which is a mutant of *Drosophila*.

Among these, amino acid sequences related to NoLS and TAT (or modified amino acid sequences thereof) are particularly preferable. For example, the CPP sequence related to NoLS as shown in SEQ ID NO: 22 and SEQ ID NO: 23 or the CPP sequence related to TAT and ANT as shown in SEQ ID NOs: 9 to 26 can be suitably used to construct the synthetic peptide disclosed here.

A peptide chain (amino acid sequence) of the synthetic peptide disclosed here may include
 (1) the CTLA4-SP-related sequence, and
 (2) the CPP-related sequence
as described above, and for example, the CPP-related sequence may be arranged on the N-terminal side or C-terminal side relative to the CTLA4-SP-related sequence.

In addition, preferably, the CPP-related sequence is arranged adjacent to the N-terminal side or C-terminal side of the CTLA4-SP-related sequence.

Specifically, there are preferably no amino acid residues other than the amino acid residues that are included in the CTLA4-SP-related sequence part and the CPP-related sequence part, between these two sequences. Alternatively, even if a linker is present, the linker connecting the above two sequences is preferably composed of 10 or less (more preferably 5 or less, for example, one or two) amino acid residues.

As long as the antitumor activity with which proliferation of at least one type of tumor cells can be inhibited is not impaired, a sequence (amino acid residue) part other than the amino acid sequences constituting the CTLA4-SP-related sequence and the CPP-related sequence can be contained.

In the synthetic peptide disclosed here, a total number of amino acid residues constituting the peptide chain is suitably 100 or less, preferably 80 or less, and preferably 70 or less (for example, preferably a peptide chain of about 40 to 60). Such a peptide with a short chain length is easily chemically synthesized and a synthetic peptide can be easily provided. Although not particularly limited, a linear or helical form is preferable because it is less likely to become an immunogen (antigen). A peptide in such a form is less likely to constitute an epitope.

A proportion of the CTLA4-SP-related sequence and the CPP-related sequence with respect to the total number of amino acid sequences of the synthesized peptide is not particularly limited as long as the antitumor activity is not impaired, but the proportion is desirably about 60 number % or more, 70 number % or more, or 80 number % or more, and preferably 90 number % or more. Here, it is preferable that all amino acid residues be L-amino acids. However, some or all of amino acid residues may be replaced with D-amino acids as long as the antitumor activity is not impaired.

Preferably, in the synthetic peptide disclosed here, at least one amino acid residue is preferably amidated. When a carboxyl group of an amino acid residue (typically, a C-terminal amino acid residue of the peptide chain) is amidated, it is possible to improve structural stability (for example, protease resistance) of the synthetic peptide. For example, when a CPP-related sequence constitutes a C-terminal of the synthetic peptide, the C-terminal amino acid residue of the sequence is preferably amidated. On the other hand, when a CTLA4-SP-related sequence constitutes a C-terminal of the synthetic peptide, the C-terminal amino acid residue of the sequence is preferably amidated. In another preferable aspect, for example, the stability of the synthetic peptide can be improved by amidating the C-terminal amino acid residue of the synthetic peptide having amino acid sequences of SEQ ID NOs: 9 to 26.

The synthetic peptide disclosed here can be easily produced according to a general chemical synthesis method. For example, any of conventionally known solid-phase synthesis methods and liquid-phase synthesis methods may be used. A solid-phase synthesis method in which t-butyloxycarbonyl (Boc) or 9-fluorenylmethoxycarbonyl (Fmoc) is applied as a protecting group of an amino group is suitable.

Regarding the synthetic peptide disclosed here, a peptide chain having a desired amino acid sequence and a modified (C-terminal amidation, etc.) part can be synthesized according to a solid-phase synthesis method using a commercially available peptide synthesizer.

Alternatively, a synthetic peptide may be produced through biosynthesis based on a genetic engineering technique. That is, a polynucleotide (typically, DNA) of a nucleotide sequence (including an ATG start codon) that encodes an amino acid sequence of a desired synthetic peptide is synthesized. Then, a recombinant vector having a gene construct for expression composed of the synthesized polynucleotide (DNA) and various regulatory elements (including promoters, ribosome binding sites, terminators, enhancers, and various cis elements that control an expression level) for expressing the amino acid sequence in host cells is constructed according to host cells.

According to a general technique, the recombinant vector is introduced into predetermined host cells (for example yeast, insect cells, and plant cells), and the host cells or tissues or subjects containing the cells are cultured under predetermined conditions. Accordingly, desired peptides can be expressed and produced in cells. Then, peptides are isolated from host cells (in a culture medium if secreted), and as necessary, refolding, purification, and the like are performed, and thereby a desired synthetic peptide can be obtained.

Here, regarding a method of constructing a recombinant vector, a method of introducing a constructed recombinant vector into host cells, and the like, methods conventionally used in the field may be directly used, and such methods themselves do not particularly characterize the present invention, and thus detailed description thereof will be omitted.

Alternatively, a template DNA (that is, a synthetic gene fragment including a nucleotide sequence that encodes an amino acid sequence of a synthetic peptide) for a cell-free protein synthesis system is constructed, various compounds (ATP, RNA polymerase, amino acids, and the like) necessary for peptide synthesis are used, and thus a desired polypeptide can be synthesized in vitro using a so-called cell-free protein synthesis system. Regarding the cell-free protein synthesis system, for example, a paper written by Shimizu et al. (Shimizu et al., Nature Biotechnology, 19, 751-755 (2001)), and a paper written by Madin et al. (Madin et al., Proc. Natl. Acad. Sci. USA, 97(2), 559-564 (2000)) can be referred to. Based on the techniques described in these papers, many companies had already commissioned polypeptides at the time of filing of this application, and cell-free protein synthesis kits (for example, commercially available from CellFree Sciences Co., Ltd., Japan) were commercially available.

A single-stranded or double-stranded polynucleotide including a nucleotide sequence that encodes the synthetic peptide disclosed here and/or a nucleotide sequence complementary to the sequence can be easily produced (synthesized) by conventionally known methods. That is, when codons corresponding to amino acid residues constituting a designed amino acid sequence are selected, a nucleotide sequence corresponding to the amino acid sequence of the synthetic peptide is easily determined and provided. Then, once the nucleotide sequence is determined, a (single-stranded) polynucleotide corresponding to a desired nucleotide sequence can be easily obtained using a DNA synthesizer or the like. In addition, desired double-stranded DNA can be obtained using the obtained single-stranded DNA as a template according to various enzymatic synthesis techniques (typically, PCR). In addition, the polynucleotide may be in the form of DNA or in the form of RNA (mRNA, etc.). Double-stranded or single-stranded DNA may be provided. When single-stranded DNA is provided, it may be a coding strand (sense strand) or a non-coding strand (antisense strand) of a sequence complementary thereto.

The polynucleotide obtained in this manner can be used as a material for constructing a recombinant gene (expression cassette) for synthetic peptide production in various host cells or a cell-free protein synthesis system as described above.

The synthetic peptide disclosed here can be suitably used as an effective component of a composition for inhibiting (or suppressing) proliferation of tumor cells (that is, a pharmaceutical antitumor composition such as an antitumor agent). Here, the synthetic peptide may be in a salt form as long as the antitumor activity is not impaired. For example, an acid addition salt of the synthetic peptide that can be obtained by an addition reaction of an inorganic acid or organic acid that is generally used according to a general method can be used. Therefore, "peptide" described in this specification and the claims includes such salt forms.

The antitumor composition disclosed here can contain various pharmaceutically (pharmacologically) acceptable carriers according to the usage form as long as the antitumor activity of the synthetic peptide as an effective component is not impaired. For example, carriers that are generally used in a peptide drug can be applied as a diluent, an excipient, and the like.

The carrier may appropriately vary depending on applications and forms of the antitumor composition disclosed here, but typically, water, a physiological buffer solution, and various organic solvents may be exemplified. The carrier may be a non-drying oil such as an aqueous solution containing an alcohol (such as ethanol) with an appropriate concentration, glycerol, and olive oil. Alternatively, it may be a liposome. In addition, examples of a secondary component that can be contained in the antitumor composition include various fillers, extending agents, binders, moisturizers, surfactants, pigments, and perfumes.

Examples of typical forms of the antitumor composition (antitumor agent) include solutions, suspensions, emulsions, aerosols, foams, granules, powders, tablets, capsules, ointments, and aqueous gels. In addition, for use in injection or the like, lyophilizates and granules for preparing a drug solution by dissolving them in saline or a suitable buffer solution (for example, PBS) immediately before use can be provided.

Here, a process itself of preparing various forms of compositions (drugs) including the synthetic peptide (main component) and various carriers (minor component) as materials may be performed according to a conventional known method, and such a production method itself does not characterize the present invention, and thus detailed description thereof will be omitted. Examples of detailed sources of information on formulation include Comprehensive Medicinal Chemistry, edited by Corwin Hansch, Pergamon Press (1990). The entire content of this book is incorporated by reference in this specification.

Cells to which the antitumor composition (synthetic peptide) disclosed here are applied are not particularly limited as long as they are tumor cells (cancer cells), and the antitumor composition can be applied to various kinds of tumor cells that occur in humans or non-human mammals. For example, many types of squamous cell carcinoma and adenocarcinoma are included. For example, cancer cells of stomach cancer, lung cancer (non-small cell lung cancer, small cell lung cancer, alveolar basal epithelial adenocarcinoma, and the like), breast cancer, melanoma and the like or cells of kidney cancer, liver cancer, colon cancer, pancreatic cancer, skin cancer such as basal cell carcinoma, neuroblastoma, retinoblastoma, pheochromocytoma, and other cell tumors may be exemplified.

Regarding cancer treatment methods in recent years, in addition to so-called "three main treatment methods for cancer (a surgical treatment, radiation therapy, and a chemical treatment)", "immunotherapy" can be used. In clinical practice, the optimal treatment method found by examining the species and stage of cancer, and the like is used, but in some cases, treatment methods that patients can select may be limited. Thus, effective therapeutic agents may differ depending on the type of cancer, and the like.

For example, regarding a melanoma treatment, a surgical treatment for removing the tumor site may be used when a melanoma is in an initial stage. However, since a melanoma is highly metastatic, it may be unresectable when detected. In addition, regarding stomach cancer treatments, a surgical treatment and a chemical treatment can be typically used. On the other hand, the radiation therapy is not generally used. It is said that the radiation therapy for stomach cancer has poor treatment results.

The antitumor composition (synthetic peptide) disclosed here can be preferably applied to melanoma cells, stomach cancer cells, and the like. This can provide more therapeutic agent options for a melanoma and stomach cancer.

The antitumor composition disclosed here can be used according to a method and in a dose depending on its form and purpose as in a conventional peptide formulation. For example, only a desired amount of the antitumor composition in the form of a solution can be administered to affected parts (typically, malignant tumor tissues) of patients (that is, living organisms) through intravenous, intramuscular, subcutaneous, intradermal or intraperitoneal injection. Alternatively, a solid form such as a tablet or a gel-like or aqueous jelly-like form such as an ointment can be directly administered to predetermined tissues (that is, an affected part such as tissues and organs including tumor cells). Alternatively, a solid form such as a tablet can be administered orally. In the case of oral administration, in order to prevent digestive enzyme decomposition in the digestive tract, encapsulation or a protective (coating) material is preferably applied.

Alternatively, with respect to tumor cells (including culture cell lines and cell masses, tissues or organs extracted from living bodies) cultured outside a living organism (in vitro), an appropriate amount of the antitumor composition disclosed here (that is, an appropriate amount of the synthetic peptide) may be supplied to a culture medium containing target culture cells (tissue and the like) at least once. The amount supplied each time and the number of times it is supplied are not particularly limited because they can vary depending on conditions such as the type of tumor cells to be cultured, the cell density (cell density when the culture starts), passage number, culture conditions, and the type of the culture medium. However, the antitumor composition is preferably added once, twice, or more so that the concentration of the synthetic peptide in the culture medium is within a range of about 0.5 µM or more and 100 µM or less, preferably within a range of 3 µM or more and 50 µM or less (for example, 6.25 µM or more and 25 µM or less).

The in vitro antitumor activity evaluation method of the antitumor composition disclosed here is not particularly limited. However, for example, an evaluation method using a test using a reagent for measuring cell proliferation using a tetrazolium salt may be exemplified.

According to the above test, for example, it is possible to calculate a cell viability (or a cell proliferation rate) when tumor cells to be evaluated are cultured using a culture solution to which the antitumor composition (synthetic peptide) disclosed here is added (that is, a culture solution containing the antitumor peptide disclosed here) for a predetermined time (for example, 24 to 72 hours). The cell viability is preferably 70% (for example, 60%, 50%, 40% or 30%) or less. Here, a specific method of calculating a cell viability will be described in the following examples.

Alternatively, in another aspect, tumor-cell-selective antitumor activity of the antitumor composition disclosed here is evaluated. Examples of a method of evaluating tumor-cell-selective antitumor activity include an evaluation method by comparing cell viabilities of the tumor cells cultured using a culture solution to which the antitumor composition (synthetic peptide) disclosed here is added for the predetermined time, and normal cells.

Specifically, for example, first, tumor cells and normal cells are cultured for the same time in the presence of antitumor peptides having the same concentration. Next, a cell viability A of tumor cells and a cell viability B of normal cells are calculated using the above reagent for measuring cell proliferation. Then, based on these cell viabilities, a specific cell viability is calculated with the following Formula (1):

$$\text{Specific cell viability} = A/B \quad (1).$$

The specific cell viability is preferably 0.6 (0.5, 0.4 or 0.3) or less. Here, the specific cell viability represented by the above Formula (1) may be multiplied by 100 for convenience. In this case, the specific cell viability is preferably 60 (50, 40 or 30) or less.

While some examples of the present invention will be described below, the present invention is not intended to be limited to those shown in the examples.

Test Example 1: Synthesis of Peptide

One type of sample peptide shown in Table 1 was produced using a commercially available peptide synthesizer. Specifically, details are as follows.

Sample 1 was designed as one example. Sample 1 was a synthetic peptide including an amino acid sequence constituting a signal peptide of human CTLA4 shown in SEQ ID NO: 1 as a CTLA4-SP-related sequence and an amino acid sequence (LIM kinase 2) shown in SEQ ID NO: 22 as a CPP-related sequence. In Sample 1, the amino acid sequence shown in SEQ ID NO: 22 was arranged adjacent to the C-terminal side of the amino acid sequence shown in SEQ ID NO: 1 (SEQ ID NO: 27).

TABLE 1

Table 1: Test sample peptide

| Sample No. | Amino acid sequence | Number of amino acid residues | SEQ ID NO: |
|---|---|---|---|
| 1 | MACLGFQRHKAQLNLAT RTWPCTLLFFLLFIPVF CKKRTLRKTDRKKR | 48 | 27 |

Sample 1 was synthesized by performing a solid-phase synthesis method (Fmoc method) manually using a commercially available peptide synthesizer. Here, since a manner of use of the peptide synthesizer itself does not characterize the present invention, detailed description thereof will be omitted. Here, in synthetic peptides shown in Table 1, in the peptide having an amino acid sequence shown in SEQ ID NO: 27, a carboxyl group (—COOH) of the C-terminal amino acid residue was amidated (—CONH$_2$).

The synthesized Sample 1 was dissolved in DMSO (dimethyl sulfoxide), and a stock solution (concentration of 2.5 mM) containing Sample 1 was prepared.

Test Example 2: Evaluation Test of Antitumor Activity of Sample 1

The antitumor activity of Sample 1 synthesized in the above Test Example 1 with respect to human-derived cultured tumor cells was evaluated.

Test Cells

Currently commercially available human gastric cancer cell lines (FU97), human alveolar basal epithelial adenocarcinoma cell lines (A549), human breast cancer cell lines (MDA-MB-231), and human melanoma cell lines (A375) were prepared as test tumor cells. In addition, normal human mammary epithelial cell culture lines (MCF-12F) were prepared for comparison.

Culture solutions for respective cells are as follows.

(1) Human Gastric Cancer Cell Lines (FU97):
A DMEM culture medium including 10 µg/mL of insulin, 50 unit/mL of penicillin, 50 µg/mL of streptomycin, and 10% fetal bovine serum (FBS) (product, commercially available from Wako Pure Chemical Industries, Ltd.)

(2) Human Alveolar Basal Epithelial Adenocarcinoma Cell Lines (A549):
An RPMI-1640 culture medium including 2 mM of L-glutamine, 1 mM of sodium pyruvate, 10 mM of HEPES, 4,500 mg/mL of glucose, 50 unit/mL of penicillin, 50 µg/mL of streptomycin, and 10% FBS (product, commercially available from Wako Pure Chemical Industries, Ltd.).

(3) Human Breast Cancer Cell Lines (MDA-MB-231):
A DMEM culture medium including 0.1 mM of non-essential amino acids, 50 unit/mL of penicillin, 50 µg/mL of streptomycin, and 10% FBS.

(4) Human Melanoma Cell Lines (A375):
A DMEM culture medium including 50 unit/mL of penicillin, 50 µg/mL of streptomycin, and 10% FBS.

(5) Normal Human Mammary Epithelial Cell Culture Line (MCF-12F):

A DMEM/F12 culture medium including 20 ng/mL of recombinant EGF, 10 μg/mL of insulin, 0.5 μg/mL of hydrocortisone, and 10% FBS (product, commercially available from Wako Pure Chemical Industries, Ltd.).

Test Areas

In this experiment, a comparative test area and peptide addition areas shown in the following Table 2 were set for each of the above five types of cell lines.

TABLE 2

| Test area for evaluation test | | | |
|---|---|---|---|
| Test area | | Add Sample 1 to culture solution | Concentration of Sample 1 in culture solution (μM) |
| Comparative test area | | No | — |
| Peptide addition area | Test area 1 | Yes | 6.25 |
| | Test area 2 | | 12.5 |
| | Test area 3 | | 25 |

Regarding the comparative test area, test areas in which cell lines to be evaluated were cultured were provided using a culture solution to which no Sample 1 was added (that is, a culture solution containing no Sample 1).

Regarding the peptide addition area, test areas in which cell lines to be evaluated were cultured were provided using a culture solution to which Sample 1 was added (that is, a culture solution containing Sample 1). In addition, the test area 1, the test area 2 and the test area 3 were provided in the peptide addition area.

Test area 1: a test area in which the concentration of Sample 1 in the culture solution was 6.25 μM.
Test area 2: a test area in which the concentration of Sample 1 in the culture solution was 12.5 μM.
Test area 3: a test area in which the concentration of Sample 1 in the culture solution was 25 μM.

Cell Culture in Presence of Sample Peptide

The above five types of cell lines were cultured in respective designated culture solutions. The cell lines were cultured so that the number of cells per well in a 96-hole (well) plate was about $5 \times 10^3$. Here, an amount of the culture solution per well was 100 μL.

The 96-well plate was then placed in a $CO_2$ incubator. Then, pre-incubation was performed under conditions of 37° C. and 5% $CO_2$ for about 1 day (about 23 hours).

Then, regarding the culture solution for the peptide addition area, culture solutions containing Sample 1 for each concentration were prepared so that the concentration of Sample 1 was 6.25 μM, 12.5 μM or 25 μM and supplied to wells (that is, wells after the pre-incubation) in which 90 μL of cells to be evaluated were cultured in each well. On the other hand, regarding the culture solution for the comparative test area, a culture solution to which no Sample 1 was added was prepared, and supplied to wells (that is, wells after the pre-incubation) in which 90 μL of cells to be evaluated were cultured in each well.

The 96-well plate was then placed in a $CO_2$ incubator, and incubated under conditions of 37° C. and 5% $CO_2$ for 48 hours.

Here, in the peptide addition areas, the numbers of test culture wells (n) in the test areas were all set to 3. Therefore, the value of the result shown in the following Table 3 is an average value of the results obtained in 3 test wells.

Further, the cell viability was calculated according to the following procedures.

Calculation of Cell Viability

After the incubation for 48 hours, the culture solution in each well was replaced with 100 of a fresh culture solution containing no Sample 1. Then, 10 μL of a cell proliferation measurement reagent "Cell Counting Kit-8" (product, commercially available from Dojindo Laboratories) containing a "water-soluble tetrazolium salt (WST-8)" as a coloring reagent was added to each well.

The 96-well plate was then placed in a $CO_2$ incubator and incubated under conditions of 37° C. and 5% $CO_2$ for 1.5 hours.

After the incubation for 1.5 hours, the culture solution to which the reagent was added was collected. Then, the absorbance at a wavelength of 450 nm (value corrected by the absorbance at a wavelength of 620 nm: A450-A620) was measured based on the reduction of the tetrazolium salt in the culture solution. Then, the cell viability was calculated according to a colorimetric method.

In the test areas (test areas 1 to 3) in the peptide addition area, the cell viability of each of the above five types of cell lines was calculated as a relative value when a measured value (measurement absorbance) of the comparative test area in the same cell lines was set as 100%. That is, regarding each of the above five types of cell lines, the cell viability (%) was calculated by dividing the measurement absorbance of the test areas (test areas 1 to 3) in the peptide addition area by the measurement absorbance of the comparative test area in the same cell lines and multiplying by 100. The results are shown in Table 3.

TABLE 3

| | | Cell viability (%) of test cells | | | | |
|---|---|---|---|---|---|---|
| Test area | Concentration of Sample 1 (μM) | FU97 | A549 | MDA-MB-231 | A375 | MCF-12F |
| 1 | 6.25 | 29.4 | 64.7 | 67.8 | 57.8 | 130.4 |
| 2 | 12.5 | 26.3 | 41.1 | 54.7 | 40.8 | 114.2 |
| 3 | 25 | 30 | 24.9 | 41.6 | 31.6 | 82 |

As shown in Table 3, it was confirmed that Sample 1 had high antitumor activity for the tumor cells supplied in this test example. In addition, it was confirmed that Sample 1 had better antitumor activity particularly for stomach cancer.

In addition, it was found that, comparing the cell viability of the tumor cells with the cell viability of MCF-12F cells as normal cells, Sample 1 had selective proliferation inhibitory activity (that is, tumor cell-selective antitumor activity) for tumor cells. Then, in order to evaluate the tumor cell-selective antitumor activity, the following specific cell viability was calculated.

Calculation of Specific Cell Viability

Specifically, the specific cell viability in the test area (that is, the test area 2) under conditions in which the concentration of Sample 1 was 12.5 μM was calculated based on the following formula:

Specific cell viability=(cell viability of test tumor cells)/(cell viability of MCF-12F cells)×100.

The results are shown in Table 4.

TABLE 4

| | Specific cell viability of test tumor cells | | | | |
|---|---|---|---|---|---|
| Test area | Concentration of Sample 1 (μM) | FU97 | A549 | MDA-MB-231 | A375 |
| 2 | 12.5 | 23.0 | 36.0 | 47.9 | 35.7 |

As shown in Table 4, in the test area 2, it was confirmed that Sample 1 had excellent tumor cell-selective antitumor activity for all of the test tumor cells.

The above test results showed that Sample 1 had excellent antitumor activity and tumor cell-selective antitumor activity for all of the tumor cells supplied in this test. This indicates that the antitumor peptide disclosed here can inhibit proliferation of tumor cells in humans.

Here, although detailed data is not shown, it was confirmed that, even if tumor cells derived from non-human mammals were used as targets, high antitumor activity and tumor cell-selective antitumor activity of Sample 1 were exhibited. In addition, the antitumor peptide disclosed here had excellent antitumor activity and tumor cell-selective antitumor activity for various tumor cells even if a CTLA4-SP-related sequence was composed of sequences derived from non-human mammals (that is, a CTLA4-SP-related sequence was composed of amino acid sequences shown in SEQ ID NOs: 2 to 8).

As described above, according to the synthetic peptide disclosed here, it is possible to selectively inhibit (or suppress) proliferation of tumor cells. Therefore, when the synthetic peptide provided by the present invention is used, it is possible to provide an antitumor composition (antitumor agent) that inhibits proliferation of at least one type of tumor cells.

The invention claimed is:

1. A synthetic peptide that inhibits proliferation of stomach cancer, lung cancer, breast cancer, or melanoma, the synthetic peptide comprising
   an amino acid sequence represented by SEQ ID NO: 1, and a CPP-related sequence consisting of a polyarginine or an amino acid sequence represented by any one of SEQ ID NOs: 9 to 26,
   wherein
   the synthetic peptide has a total number of amino acid residues of 100 or less and
   the CPP-related sequence is arranged on the N-terminal side or C-terminal side of the amino acid sequence represented by SEQ ID NO: 1 in an adjacent manner or via a linker consisting of one or two amino acid residues.

2. The synthetic peptide according to claim 1, wherein the CPP-related sequence is an amino acid sequence represented by SEQ ID NO: 22.

3. The synthetic peptide according to claim 1, comprising an amino acid sequence represented by SEQ ID NO: 27.

4. An antitumor composition that inhibits proliferation of tumor cells of stomach cancer, lung cancer, breast cancer, or melanoma, the antitumor composition comprising: the synthetic peptide according to claim 1 and at least one pharmaceutically acceptable carrier.

5. The synthetic peptide according to claim 1, wherein the amino acid sequence represented by SEQ ID NO: 1 is directly linked to the CPP-related sequence without the linker.

6. The synthetic peptide according to claim 1, wherein the amino acid sequence represented by SEQ ID NO: 1 is directly linked to the amino acid sequence represented by SEQ ID NO: 22 without the linker.

7. The antitumor composition according to claim 4, wherein the amino acid sequence represented by SEQ ID NO: 1 is directly linked to the CPP-related sequence without the linker.

8. The antitumor composition according to claim 4, wherein the amino acid sequence represented by SEQ ID NO: 1 is directly linked to the amino acid sequence represented by SEQ ID NO: 22 without the linker.

* * * * *

SEQUENCE LISTING

```
<160> NUMBER OF SEQ ID NOS: 27

<210> SEQ ID NO 1
<211> LENGTH: 35
<212> TYPE: PRT
<213> ORGANISM: Homo sapiens

<400> SEQUENCE: 1

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys
        35

<210> SEQ ID NO 2
<211> LENGTH: 35
<212> TYPE: PRT
<213> ORGANISM: Canis familiaris

<400> SEQUENCE: 2

Met Ala Gly Phe Gly Phe Arg Arg His Gly Val Gln Pro Asp Leu Ala
1               5                   10                  15

Ser Arg Thr Trp Pro Cys Thr Ala Leu Phe Ser Leu Leu Phe Ile Pro
            20                  25                  30

Val Phe Ser
        35

<210> SEQ ID NO 3
<211> LENGTH: 35
<212> TYPE: PRT
<213> ORGANISM: Mus musculus

<400> SEQUENCE: 3

Met Ala Cys Leu Gly Leu Arg Arg Tyr Lys Ala Gln Leu Gln Leu Pro
1               5                   10                  15

Ser Arg Thr Trp Pro Phe Val Ala Leu Leu Thr Leu Leu Phe Ile Pro
            20                  25                  30

Val Phe Ser
        35

<210> SEQ ID NO 4
```

```
<211> LENGTH: 35
<212> TYPE: PRT
<213> ORGANISM: Oryctolagus cuniculus

<400> SEQUENCE: 4

Met Ala Arg Leu Gly Phe Gln Arg Gln Gly Thr Gln Leu Asp Leu Ala
1               5                   10                  15

Ser Arg Thr Trp Ser Cys Ala Ala Leu Phe Ser Leu Leu Phe Leu Pro
            20                  25                  30

Val Phe Ser
        35

<210> SEQ ID NO 5
<211> LENGTH: 35
<212> TYPE: PRT
<213> ORGANISM: Sus scrofa

<400> SEQUENCE: 5

Met Ala Cys Ser Gly Phe Gln Ser His Gly Ala Trp Leu Glu Leu Thr
1               5                   10                  15

Ser Arg Thr Trp Pro Cys Thr Ala Leu Phe Ser Leu Leu Phe Ile Pro
            20                  25                  30

Val Phe Ser
        35

<210> SEQ ID NO 6
<211> LENGTH: 37
<212> TYPE: PRT
<213> ORGANISM: Aotus trivirgatus

<400> SEQUENCE: 6

Met Ala Cys Leu Gly Phe Gln Arg His Lys Ala Gln Leu Asp Leu Ala
1               5                   10                  15

Thr Arg Thr Trp Pro Cys Thr Phe Leu Phe Ser Leu Leu Phe Ile Leu
            20                  25                  30

Val Phe Ser Asn Ala
        35

<210> SEQ ID NO 7
<211> LENGTH: 37
<212> TYPE: PRT
<213> ORGANISM: Papio anubis

<400> SEQUENCE: 7

Met Ala Cys Leu Gly Phe Gln Arg His Lys Ala Gln Leu Asn Leu Ala
1               5                   10                  15

Thr Arg Thr Arg Pro Tyr Thr Leu Leu Phe Ser Leu Leu Phe Ile Pro
            20                  25                  30

Val Phe Ser Lys Ala
        35

<210> SEQ ID NO 8
<211> LENGTH: 37
<212> TYPE: PRT
<213> ORGANISM: Macaca mulatta

<400> SEQUENCE: 8

Met Ala Cys Leu Gly Phe Gln Arg His Lys Ala Arg Leu Asn Leu Ala
1               5                   10                  15

Thr Arg Thr Arg Pro Tyr Thr Leu Leu Phe Ser Leu Leu Phe Ile Pro
            20                  25                  30
```

Val Phe Ser Lys Ala
        35

<210> SEQ ID NO 9
<211> LENGTH: 14
<212> TYPE: PRT
<213> ORGANISM: Artificial Sequence
<220> FEATURE:
<223> OTHER INFORMATION: synthetic peptide

<400> SEQUENCE: 9

Arg Ser Arg Lys Tyr Thr Ser Trp Tyr Val Ala Leu Lys Arg
1               5                   10

<210> SEQ ID NO 10
<211> LENGTH: 19
<212> TYPE: PRT
<213> ORGANISM: Artificial Sequence
<220> FEATURE:
<223> OTHER INFORMATION: synthetic peptide

<400> SEQUENCE: 10

Met Ala Lys Ser Ile Arg Ser Lys His Arg Arg Gln Met Arg Met Met
1               5                   10                  15

Lys Arg Glu

<210> SEQ ID NO 11
<211> LENGTH: 16
<212> TYPE: PRT
<213> ORGANISM: Artificial Sequence
<220> FEATURE:
<223> OTHER INFORMATION: synthetic peptide

<400> SEQUENCE: 11

Met Ala Arg Arg Arg Arg His Arg Gly Pro Arg Arg Pro Arg Pro Pro
1               5                   10                  15

<210> SEQ ID NO 12
<211> LENGTH: 19
<212> TYPE: PRT
<213> ORGANISM: Artificial Sequence
<220> FEATURE:
<223> OTHER INFORMATION: synthetic peptide

<400> SEQUENCE: 12

Gly Arg Cys Arg Arg Leu Ala Asn Phe Gly Pro Arg Lys Arg Arg Arg
1               5                   10                  15

Arg Arg Arg

<210> SEQ ID NO 13
<211> LENGTH: 16
<212> TYPE: PRT
<213> ORGANISM: Artificial Sequence
<220> FEATURE:
<223> OTHER INFORMATION: synthetic peptide

<400> SEQUENCE: 13

Arg Arg Arg Lys Arg Asn Arg Asp Ala Arg Arg Arg Arg Lys Gln
1               5                   10                  15

<210> SEQ ID NO 14
<211> LENGTH: 17
<212> TYPE: PRT
<213> ORGANISM: Artificial Sequence
<220> FEATURE:

<223> OTHER INFORMATION: synthetic peptide

<400> SEQUENCE: 14

Met Gln Arg Lys Pro Thr Ile Arg Arg Lys Asn Leu Arg Leu Arg Arg
1               5                   10                  15

Lys

<210> SEQ ID NO 15
<211> LENGTH: 7
<212> TYPE: PRT
<213> ORGANISM: Artificial Sequence
<220> FEATURE:
<223> OTHER INFORMATION: synthetic peptide

<400> SEQUENCE: 15

Ile Met Arg Arg Arg Gly Leu
1               5

<210> SEQ ID NO 16
<211> LENGTH: 8
<212> TYPE: PRT
<213> ORGANISM: Artificial Sequence
<220> FEATURE:
<223> OTHER INFORMATION: synthetic peptide

<400> SEQUENCE: 16

Lys Lys Leu Lys Lys Arg Asn Lys
1               5

<210> SEQ ID NO 17
<211> LENGTH: 9
<212> TYPE: PRT
<213> ORGANISM: Artificial Sequence
<220> FEATURE:
<223> OTHER INFORMATION: synthetic peptide

<400> SEQUENCE: 17

Arg Arg Arg Ala Asn Asn Arg Arg Arg
1               5

<210> SEQ ID NO 18
<211> LENGTH: 7
<212> TYPE: PRT
<213> ORGANISM: Artificial Sequence
<220> FEATURE:
<223> OTHER INFORMATION: synthetic peptide

<400> SEQUENCE: 18

Arg Lys Lys Arg Lys Lys Lys
1               5

<210> SEQ ID NO 19
<211> LENGTH: 15
<212> TYPE: PRT
<213> ORGANISM: Artificial Sequence
<220> FEATURE:
<223> OTHER INFORMATION: synthetic peptide

<400> SEQUENCE: 19

Lys Arg Lys Gly Lys Leu Lys Asn Lys Gly Ser Lys Arg Lys Lys
1               5                   10                  15

<210> SEQ ID NO 20
<211> LENGTH: 18
<212> TYPE: PRT
<213> ORGANISM: Artificial Sequence

```
<220> FEATURE:
<223> OTHER INFORMATION: synthetic peptide

<400> SEQUENCE: 20

Ser Lys Arg Leu Ser Ser Arg Ala Arg Lys Arg Ala Ala Lys Arg Arg
1               5                   10                  15
Leu Gly

<210> SEQ ID NO 21
<211> LENGTH: 14
<212> TYPE: PRT
<213> ORGANISM: Artificial Sequence
<220> FEATURE:
<223> OTHER INFORMATION: synthetic peptide

<400> SEQUENCE: 21

Lys Arg Pro Arg Arg Arg Pro Ser Arg Pro Phe Arg Lys Pro
1               5                   10

<210> SEQ ID NO 22
<211> LENGTH: 13
<212> TYPE: PRT
<213> ORGANISM: Artificial Sequence
<220> FEATURE:
<223> OTHER INFORMATION: synthetic peptide

<400> SEQUENCE: 22

Lys Lys Arg Thr Leu Arg Lys Asn Asp Arg Lys Lys Arg
1               5                   10

<210> SEQ ID NO 23
<211> LENGTH: 8
<212> TYPE: PRT
<213> ORGANISM: Artificial Sequence
<220> FEATURE:
<223> OTHER INFORMATION: synthetic peptide

<400> SEQUENCE: 23

Trp Arg Arg Gln Ala Arg Phe Lys
1               5

<210> SEQ ID NO 24
<211> LENGTH: 9
<212> TYPE: PRT
<213> ORGANISM: Artificial Sequence
<220> FEATURE:
<223> OTHER INFORMATION: synthetic peptide

<400> SEQUENCE: 24

Arg Lys Lys Arg Arg Gln Arg Arg Arg
1               5

<210> SEQ ID NO 25
<211> LENGTH: 11
<212> TYPE: PRT
<213> ORGANISM: Artificial Sequence
<220> FEATURE:
<223> OTHER INFORMATION: synthetic peptide

<400> SEQUENCE: 25

Tyr Ala Arg Ala Ala Ala Arg Gln Ala Arg Ala
1               5                   10

<210> SEQ ID NO 26
<211> LENGTH: 18
<212> TYPE: PRT
```

```
<213> ORGANISM: Artificial Sequence
<220> FEATURE:
<223> OTHER INFORMATION: synthetic peptide

<400> SEQUENCE: 26

Lys Gly Arg Gln Val Lys Val Trp Phe Gln Asn Arg Arg Met Lys Trp
1               5                   10                  15

Lys Lys

<210> SEQ ID NO 27
<211> LENGTH: 48
<212> TYPE: PRT
<213> ORGANISM: Artificial Sequence
<220> FEATURE:
<223> OTHER INFORMATION: synthetic peptide

<400> SEQUENCE: 27

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Lys Arg Thr Leu Arg Lys Asn Asp Arg Lys Lys Arg
        35                  40                  45
```